United States Patent
Neuba et al.

(10) Patent No.: US 8,845,758 B2
(45) Date of Patent: Sep. 30, 2014

(54) MEANS TO COLOR AND/OR LIGHTEN KERATIN FIBERS WITHOUT AMMONIA ODOR

(71) Applicant: Henkel AG & Co. KGaA, Duesseldorf (DE)

(72) Inventors: Constanze Neuba, Grevenbroich (DE); Frank Jannsen, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/102,655

(22) Filed: Dec. 11, 2013

(65) Prior Publication Data

US 2014/0165298 A1 Jun. 19, 2014

(30) Foreign Application Priority Data

Dec. 14, 2012 (DE) .......................... 10 2012 223 206

(51) Int. Cl.
*A61Q 5/10* (2006.01)
*A61K 8/41* (2006.01)
*A61K 8/22* (2006.01)
*A61K 8/34* (2006.01)
*A61K 8/25* (2006.01)

(52) U.S. Cl.
CPC ... *A61K 8/41* (2013.01); *A61K 8/22* (2013.01); *A61Q 5/10* (2013.01); *A61K 8/342* (2013.01); *A61K 8/25* (2013.01)
USPC ............... 8/405; 8/550; 8/551; 8/552; 8/604; 8/611; 8/619

(58) Field of Classification Search
USPC .............. 8/405, 550, 551, 552, 604, 611, 619
See application file for complete search history.

(56) References Cited

U.S. PATENT DOCUMENTS

2012/0048288 A1* 3/2012 Reichert et al. ............... 132/208

FOREIGN PATENT DOCUMENTS

| JP | 2003-040750 A | 2/2003 |
| JP | 2007-191459 A | 8/2007 |
| WO | 2005/110499 A1 | 11/2005 |
| WO | 2006/060565 A2 | 6/2006 |
| WO | 2006/060570 A2 | 6/2006 |

* cited by examiner

*Primary Examiner* — Eisa Elhilo
(74) *Attorney, Agent, or Firm* — David K. Benson

(57) ABSTRACT

The subject of the disclosure, in an exemplary embodiment, is an agent for coloring and/or lightening keratinic fibers, in particular human hair, containing in a cosmetic carrier: (a) ammonia, (b) one or more alkanolamines from the group of monoethanolamine, 2-amino-2-methylpropanol and triethanolamine, (c) one or more alkalizing agents from the group of potassium hydroxide, sodium hydroxide, sodium silicates, and potassium silicates, (d) one or more ethoxylated fatty alcohols having a degree of ethoxylation from about 80 to about 120, (e) one or more fatty alcohols from the group of arachyl alcohol (eicosan-1-ol), gadoleyl alcohol (9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol) and brassidyl alcohol ((13E)-docosen-1-ol).

14 Claims, No Drawings

MEANS TO COLOR AND/OR LIGHTEN KERATIN FIBERS WITHOUT AMMONIA ODOR

CROSS-REFERENCE TO RELATED APPLICATIONS

This application claims priority to German Patent Application DE 10 2012 223 206.0, filed Dec. 14, 2012, the contents of which are incorporated herein by reference in their entirety.

TECHNICAL FIELD

The subject matter of the present disclosure is agents for coloring and/or lightening keratinic fibers, in particular human hair, containing in a cosmetic carrier a special combination of three types of alkalizing agents, at least one non-ionic emulsifier agent of the type of the ethoxylated fatty alcohols having a degree of ethoxylation from about 80 to about 120, and at least one special longer-chain fatty alcohol. A further subject of the present disclosure is a ready-to-use agent that is produced by mixing the aforesaid agent with a further separate component containing hydrogen peroxide.

BACKGROUND

One skilled in the art knows of a variety of coloring systems, depending on the required color result, for making available color-changing cosmetic agents, in particular for keratinic fibers such as e.g. human hair. For permanent, intense color results having corresponding fastness properties, so-called "oxidation" coloring agents are used. Such coloring agents usually contain oxidation dye precursors called "developer components" and "coupler components" that, under the influence of oxidizing agents such as hydrogen peroxide, form the actual dyes with one another. Oxidizing coloring agents are notable for outstanding, long-lasting color results. In addition to coloring, lightening of one's own hair color, resp. hair-bleaching, is a very special desire of many consumers. For this, the natural or artificial dyes coloring the fibers are usually decolorized oxidatively using corresponding oxidizing agents, for example hydrogen peroxide.

In order to provide satisfactory coloring and lightening performance, oxidative coloring agents resp. lightening agents generally require an alkaline pH during utilization; optimum results are achieved in particular at pH values between about 8.5 and about 10.5.

Until the present time, ammonia has been the alkalizing agent of choice for establishing these pH values. Not only can ammonia be used to establish the pH range necessary for dye formation, but ammonia also ensures swelling of the hair to a greater extent than all other known alkalizing agents. At the same time, ammonia acts as a penetration adjuvant.

The applications-engineering advantages associated with the use of ammonia are so numerous that despite its unpleasant, pungent odor, ammonia is used in a large number of commercial oxidative coloring agents.

Extensive efforts to reduce the ammonia odor are already known from the literature. A variety of possibilities exist for minimizing the odor: as a first possibility, the literature recites varying the alkalizing agent and thus partly or entirely replacing ammonia with odorless alternatives.

A plurality of formulations that employ a mixture of ammonia and monoethanolamine, or exclusively monoethanolamine, as an alkalizing agent already exist in the literature.

Reducing the ammonia content often results, however, in poorer penetration of the dyes into the hair, which can be reflected especially in poorer gray coverage and poorer washing fastness.

Although complete or partial replacement of ammonia with alternative alkalizing agents has advantageous effects in terms of minimizing the odor of the coloring resp. lightening agents, it is associated with disadvantages in terms of the fastness properties of the color results obtained with the coloring resp. lightening agents. If a corresponding replacement of the alkalizing agent is made, the resulting losses in terms of coloring performance must be compensated for by optimizing the formulation.

WO 2006060570 and WO 2006060565 propose the use of carbonates or carbonate sources as alkalizing agents in order to furnish oxidative coloring agents with little odor impact. It is likewise known in the literature, however, that carbonates in combination with oxidizing agents can damage the hair to a greater extent. The additional damage to the hair brought about by carbonates may not be much of a problem when utilizing the coloring agent on untreated resp. undamaged hair, but in the case of persons who regularly color resp. bleach their hair it can add up to serious cumulative damage. If more intense lightening and/or regular coloring is desired, the use of carbonates therefore once again does not represent a feasible alternative.

A second possibility, in principle, for reducing ammonia odor consists in the addition of special perfume substances that are intended to mask the ammonia odor. This approach is taken, for example, in WO 2005/110499. Perfume substances can be unstable under alkaline storage conditions, however, so that the risk exists that the scents may become degraded or structurally modified during storage, which is also reflected in an unpredictable change in odor. Because corresponding changes often become perceptible only after several months or even years, the employment of new resp. unknown perfumes is considered problematic.

A third general possibility for reducing ammonia odor consists in optimizing the formulation. The idea here is to select the carrier constituents of the formulation in such a way that they ensure optimum retention of ammonia in the formulation, and in that manner minimize its odor. It is once again known, however, that the formulation, the fatty substances contained in it, its emulsifier agents and surfactants, and its viscosity have a substantial influence on coloring performance. When the formulation is modified, a deterioration in coloring performance must therefore in all cases be avoided.

For example, JP 2007191459 proposes the use of cationic surfactants, phosphate esters, and aliphatic alcohols in order to reduce ammonia odor in hair coloring agents.

JP 2003040750 discloses that the ammonia odor in hair-bleaching agents is particularly low when at least 5% of a crystalline component is added to the agents.

Although the literature proposes several methods for reducing the odor impact caused by ammonia, there is nevertheless no known possibility for completely suppressing ammonia odor.

BRIEF SUMMARY

The object of the present disclosure was therefore to make available almost odorless agents for oxidative coloring and/or lightening of hair. To meet the performance requirements imposed on these agents, they are to contain ammonia, but the ammonia odor is to be completely masked. In particular, the complete masking of the ammonia odor is intended to persist over a long period of time, so that even after storage of the agents (in a closed vessel) for several weeks, optimally for several months, no ammonia odor is perceptible. At the same time, the agents are to exhibit no loss in terms of their coloring performance, in particular in terms of their gray coverage and their washing fastness. In addition, utilization of the agent is not to be associated with greater hair damage.

A further object of the present disclosure was to successfully mask the ammonia odor for the entire duration of use. The intention was that even after a maximum of two hours of contact, no ammonia odor—and moreover also no other chemical odor—was to be perceptible.

In the course of the work leading to this disclosure it has emerged, surprisingly, that it is possible for the ammonia contained in agents for coloring and/or lightening to be entirely masked in terms of olfaction, resp. for olfactory perception thereof to be completely prevented, when a special combination of several different alkalizing agents is employed and when these various alkalizing agents are simultaneously combined with a mixture of specially ethoxylated fatty alcohols and higher fatty alcohols.

A first subject of the present disclosure is therefore, in accordance with an exemplary embodiment, an agent for coloring and/or lightening keratinic fibers, in particular human hair, containing in a cosmetic carrier:
(a) ammonia,
(b) one or more alkanolamines from the group of monoethanolamine, 2-amino-2-methylpropanol, and triethanolamine,
(c) one or more alkalizing agents from the group of potassium hydroxide, sodium hydroxide, sodium silicates, and potassium silicates,
(d) one or more ethoxylated fatty alcohols having a degree of ethoxylation from about 80 to about 120,
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol).

This brief summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the disclosure or the application and uses of the disclosure. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the disclosure and not to limit the scope of the disclosure which is defined by the claims. Furthermore, there is no intention to be bound by any expressed or implied theory presented in the preceding technical field, background, brief summary, or the following detailed description.

"Keratin-containing fibers" are understood in principle as all animal hair, e.g. wool, horsehair, angora wool, furs, feathers, and products or textiles produced therefrom. Preferably, however, the keratinic fibers are human hairs.

The term "agents for coloring and/or lightening" keratin fibers that is used according to the present disclosure is understood to mean agents for oxidative coloring of hair and agents for oxidative lightening resp. bleaching of hair.

In order to produce color, oxidative coloring agents contain oxidation dye precursors, so-called "developers" and "coupler components." Developers and couplers diffuse separately into the keratin fibers and, under the influence of ammonia as an alkalizing agent and an oxidizing agent (usually hydrogen peroxide), react chemically with one another to form the actual dyes. Depending on the quantity of oxidizing agent employed, the keratin fibers are simultaneously lightened to a greater or less extent during coloring, since the oxidizing agent not only initiates the dye-forming process of the developers and couplers, but also oxidatively destroys the hair's own pigments (melanins). Depending on the quantities of oxidation dye precursors and oxidizing agent that are used, the oxidative coloring process can therefore involve predominantly coloring (with a high dye proportion) or predominantly lightening (with a high proportion of oxidizing agent). In the latter case, the oxidation dye precursors are employed principally to tint the lightening result.

Agents for oxidative lightening resp. bleaching of hair often contain hydrogen peroxide as the only oxidizing agent in order to achieve a moderate bleaching effect, but if there is a desire for more intense hair-bleaching performance they can also contain oxidizing agent mixtures. In the latter case hydrogen peroxide is usually employed in combination with persulfates such as potassium persulfate, sodium persulfate, and/or ammonium persulfate. Agents for oxidative lightening or bleaching can likewise additionally contain oxidation dye precursors, but the focus of these agents is on lightening.

In a preferred embodiment, the agents according to the present disclosure are agents for oxidative coloring of hair.

The agents according to the present disclosure contain the constituents essential to the disclosure in a cosmetic carrier, preferably in a suitable aqueous, alcoholic, or aqueous alcoholic carrier. For hair-coloring purposes such carriers are, for example, creams, emulsions, gels, or also surfactant-containing foaming solutions, for example shampoos, foam aerosols, foam formulations, or other preparations that are suitable for utilization on the hair.

As a first essential formulation constituent (a), the agents according to the present disclosure for coloring and/or lightening keratin fibers contain ammonia.

Ammonia is employed preferably in the form of its aqueous solution. Corresponding aqueous ammonia solutions can be about 10- to about 35-percent solutions (calculated in wt %; about 100 g aqueous ammonia solution accordingly contains about 10 to about 35 g ammonia). Ammonia is employed preferably in the form of an about 20 to about 30 wt % solution, particularly preferably in the form of an about 25 wt % solution.

In order for the agents according to the present disclosure to conform to the requirements profile imposed upon them in terms of their color intensity and their fastness properties, it is not possible to dispense with the use of ammonia. It has emerged, however, that ammonia can be completely masked olfactorily if it is contained in specific quantity ranges in the agents according to the present disclosure. Complete masking by means of the further ingredients (d) and (e) that are essential to the disclosure and are likewise contained in the agent according to the present disclosure is possible when the ready-to-use agent contains ammonia (a) in a quantity from about 0.20 to about 1.5 wt %, preferably from about 0.25 to about 1.2 wt %, more preferably from about 0.30 to about 1.0 wt %, and particularly preferably from about 0.31 to about 0.8 wt %, based on the total weight of the ready-to-use agent.

In a more preferred embodiment, an agent for coloring and/or lightening keratinic fibers is therefore characterized in that it contains ammonia (a) in a quantity from about 0.20 to about 1.5 wt %, preferably from about 0.25 to about 1.2 wt %, more preferably from about 0.30 to about 1.0 wt %, and particularly preferably from about 0.31 to about 0.8 wt %, based on the total weight of the ready-to-use agent.

The aforementioned preferred and particularly preferred quantitative indications of ammonia (a) assume pure ammonia as a basis for calculation. If about 0.31 to about 0.8 wt % ammonia (a) is therefore employed very particularly preferably in the ready-to-use agent, this corresponds to the utilization of a quantity from about 1.24 g to about 3.2 g of an about 25 wt % ammonia solution in the ready-to-use coloring agent.

When ammonia in the above-described quantity ranges is furthermore combined with the alkalizing agents (b) and (c), color results with high color intensity and outstanding fastness properties can then be generated with the corresponding agents according to the present disclosure. Surprisingly, with the use of a combination of the constituents (a) to (e) that are essential to the disclosure, not only are losses in color intensity avoided, but moreover the color results produced with these agents in fact exhibit improved gray coverage and improved washing fastness.

The agents according to the present disclosure for coloring and/or lightening keratinic fibers contain, as a second constituent (b) essential to the disclosure, one or more alkanolamines from the group of monoethanolamine (2-aminoethanol, formula A), 2-amino-2-methylpropanol (2-amino-2-methylpropan-1-ol, formula B), and triethanolamine (formula C).

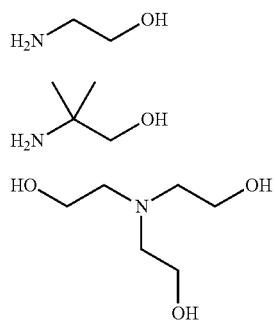

Formula A

Formula B

Formula C

In order to achieve maximum odor masking and in order to optimize fastness properties, the alkanolamine(s) is/are also preferably employed in special quantitative ranges. Complete masking of the ammonia odor, and at the same time particularly good washing fastness values, are achieved when the alkanolamines (b) are contained in a total quantity from about 0.2 to about 6.5 wt %, preferably from about 0.5 to about 4.0 wt %, more preferably from about 0.7 to about 2.5 wt %, and particularly preferably from about 0.8 to about 1.6 wt %, based on the total weight of the ready-to-use agent.

In a further preferred embodiment, an agent for coloring and/or lightening keratinic fibers is therefore characterized in that it contains one or more alkanolamines (b) from the group of monoethanolamine, 2-amino-2-methylpropanol, and triethanolamine in a total quantity from about 0.2 to about 6.5 wt %, preferably from 0.5 to 4.0 wt %, more preferably from about 0.7 to about 2.5 wt %, and particularly preferably from about 0.8 to about 1.6 wt %, based on the total weight of the ready-to-use agent.

In order to meet the stated object of the present disclosure, the agents according to the present disclosure furthermore contain one or more representatives of a third class of alkalizing agents (c) that are selected from the group of potassium hydroxide (KOH), sodium hydroxide (NaOH), sodium silicates, and potassium silicates.

Potassium hydroxide and sodium hydroxide can be used in the form of their solids. It is preferred, however, if these hydroxides are employed in the form of aqueous solutions. These aqueous solutions can be about 50 wt %, about 40 wt %, about 30 wt %, about 20 wt %, and about 10 wt % solutions; the use in the agents according to the present disclosure of an even further diluted aqueous solution is also possible.

"Sodium silicates" for purposes of the present disclosure are chemical compounds that are made up of sodium oxide and silicon dioxide and can occur in a variety of molar ratios (monosilicate, metasilicate, and polysilicate). One example of a sodium silicate is the sodium salt of orthosilicic acid having the empirical formula $Na_4SiO_4$, which is also referred to as "sodium orthosilicate."

Further examples of suitable sodium silicates are disodium metasilicate resp. sodium metasilicate having the empirical formula $Na_2SiO_3$, disodium silicate having the empirical formula $Na_2Si_2O_5$, or disodium trisilicate having the empirical formula $Na_2Si_3O_7$.

Potassium silicates are corresponding chemical compounds that are made up of potassium oxide and silicon dioxides; suitable potassium silicates are, for example, compounds having the empirical formulas $K_4SiO_4$, $K_2SiO_3$, $K_2Si_2O_5$, and $K_2Si_3O_7$.

Silicates in amorphous form can be produced by melting together silicon dioxide and alkali oxide at molar ratios between about 1:1 and about 4:1. The solids thereby obtained are dissolved at approximately about 150° C. and about 5 bar vapor pressure in order to obtain a solution of sodium silicate in water; these corresponding solutions are alkali water glasses.

"Alkali water glasses" refer to glass-like (amorphous) sodium and potassium silicates solidified from a melt, or to aqueous solutions thereof. Depending on whether predominantly sodium silicates or predominantly potassium silicates are contained, the term "sodium water glass" or "potassium water glass" is used. Sodium water glasses and potassium water glasses are also encompassed within this disclosure by the definition of "sodium silicates" and "potassium silicates."

The molar composition of water glasses is usually about 2 to about 4 mol $SiO_2$ to about 1 mol alkali oxide ($Na_2O$ or $K_2O$).

An example of a preferred sodium silicate is sodium water glass, which is present in the form of its aqueous solution, has a $Na_2O$ content from about 7.5 to about 8.8 wt % and a $SiO_2$ content from about 25.0 to about 28.5 wt %, and which has the CAS (Chemical Abstracts) number 1344-09-5.

In order to achieve the stated object of the present disclosure, however, it has proven to be particularly advantageous if, from the group constituted from potassium hydroxide (KOH), sodium hydroxide (NaOH), sodium silicates, and potassium silicates, what is selected as an alkalizing agent (c) is potassium hydroxide and/or sodium hydroxide.

In a further more preferred embodiment, an agent for coloring and/or lightening keratinic fibers is therefore characterized in that it contains sodium hydroxide and/or potassium hydroxide as an alkalizing agent (c).

Of the two alkalizing agents (c) potassium hydroxide and sodium hydroxide, potassium hydroxide is once again very particularly preferred.

In a further embodiment that is explicitly very particularly preferred, an agent for coloring and/or lightening keratinic fibers is therefore characterized in that it contains potassium hydroxide as an alkalizing agent (c).

The agents according to the present disclosure are, in particular, particularly suitable when the representatives of the third class of alkalizing agents (c), which are selected from the group of potassium hydroxide (KOH), sodium hydroxide (NaOH), sodium silicates, and potassium silicates, are also employed in special quantity ranges coordinated with the other two alkalizing agent classes (a) and (b).

In a further very particularly preferred embodiment, an agent for coloring and/or lightening keratinic fibers is therefore characterized in that it contains one or more alkalizing agents (c) from the group of potassium hydroxide, sodium hydroxide, sodium silicates, and potassium silicates in a total quantity from about 0.1 to about 2.5 wt %, preferably from about 0.15 to about 1.5 wt %, more preferably from about 0.2 to about 1.0 wt %, and particularly preferably from about 0.25 to about 0.5 wt %, based on the total weight of the ready-to-use agent.

A preferred agent according to the present disclosure contains, in a cosmetic carrier,
(a) about 0.20 to about 1.5 wt % ammonia,
(b) about 0.2 to about 6.5 wt % monoethanolamine,
(c) about 0.1 to about 2.5 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.20 to about 1.5 wt % ammonia,
(b) about 0.2 to about 6.5 wt % monoethanolamine,
(c) about 0.1 to about 2.5 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.20 to about 1.5 wt % ammonia,
(b) about 0.2 to about 6.5 wt % 2-amino-2-methylpropanol,
(c) about 0.1 to about 2.5 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.20 to about 1.5 wt % ammonia,
(b) about 0.2 to about 6.5 wt % 2-amino-2-methylpropanol,
(c) about 0.1 to about 2.5 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.25 to about 1.2 wt % ammonia,
(b) about 0.5 to about 4.0 wt % monoethanolamine,
(c) about 0.15 to about 1.5 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.25 to about 1.2 wt % ammonia,
(b) about 0.5 to about 4.0 wt % monoethanolamine,
(c) about 0.15 to about 1.5 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.25 to about 1.2 wt % ammonia,
(b) about 0.5 to about 4.0 wt % 2-amino-2-methylpropanol,
(c) about 0.15 to about 1.5 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.25 to about 1.2 wt % ammonia,
(b) about 0.5 to about 4.0 wt % 2-amino-2-methylpropanol,
(c) about 0.15 to about 1.5 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.30 to about 1.0 wt % ammonia,
(b) about 0.7 to about 2.5 wt % monoethanolamine,
(c) about 0.2 to about 1.0 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.30 to about 1.0 wt % ammonia,
(b) about 0.7 to about 2.5 wt % monoethanolamine,
(c) about 0.2 to about 1.0 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.30 to about 1.0 wt % ammonia,
(b) about 0.7 to about 2.5 wt % 2-amino-2-methylpropanol,
(c) about 0.2 to about 1.0 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.30 to about 1.0 wt % ammonia,
(b) about 0.7 to about 2.5 wt % 2-amino-2-methylpropanol,
(c) about 0.2 to about 1.0 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.35 to about 0.8 wt % ammonia,
(b) about 0.8 to about 1.6 wt % monoethanolamine,
(c) about 0.25 to about 0.5 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.35 to about 0.8 wt % ammonia,
(b) about 0.8 to about 1.6 wt % monoethanolamine,
(c) about 0.25 to about 0.5 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.35 to about 0.8 wt % ammonia,
(b) about 0.8 to about 1.6 wt % 2-amino-2-methylpropanol,
(c) about 0.25 to about 0.5 wt % potassium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

A further preferred agent according to the present disclosure contains, in a cosmetic carrier,
(a) about 0.35 to about 0.8 wt % ammonia,
(b) about 0.8 to about 1.6 wt % 2-amino-2-methylpropanol,
(c) about 0.25 to about 0.5 wt % sodium hydroxide,
(d) one or more ethoxylated fatty alcohols having a degree of ethoxylation from about 80 to about 120, and
(e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), all quantity indications being based on the total weight of the ready-to-use agent.

As a fourth formulation constituent (d) essential to the disclosure, the agents according to the present disclosure contain one or more ethoxylated fatty alcohols having a degree of ethoxylation from about 80 to about 120.

"Fatty alcohols" are to be understood according to the present disclosure as saturated or unsaturated, unbranched or branched $C_8$ to $C_{28}$ alkyl groups with hydroxy substitution. Unsaturated fatty alcohols can be mono- or polyunsaturated. In the case of an unsaturated fatty alcohol, its carbon-carbon double bond(s) can exhibit the cis- or trans-configuration.

Preferred fatty alcohols are octan-1-ol (octyl alcohol, capryl alcohol), decan-1-ol (decyl alcohol, caprinyl alcohol), dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), eicosan-1-ol (eicosyl alcohol, arachyl alcohol), (9Z)-eicos-9-en-1-ol (gadoleyl alcohol), (5Z,8Z,11Z,14Z)-eicosa-5,8,11,14-tetraen-1-ol (arachidonyl alcohol), docosan-1-ol (docosyl alcohol, behenyl alcohol), (13E)-docosen-1-ol (brassidyl alcohol), and (13Z)-docos-13-en-1-ol (erucyl alcohol). Within this group in turn, hexadecan-1-ol (hexadecyl alcohol, cetyl alcohol, palmityl alcohol) and octadecan-1-ol (octadecyl alcohol, stearyl alcohol) are very particularly preferred fatty alcohols.

In order to constitute the constituent (d) essential to the present disclosure, these fatty alcohols are ethoxylated with a degree of ethoxylation from about 80 to about 120.

"Ethoxylation" (also "oxyethylation") is understood as the reaction of fatty alcohols with ethylene oxide (EO). The insertion of from about 80 to about 120 groups of the —CH$_2$—CH$_2$—O— type per fatty alcohol molecule yields linear polyethers that carry at one end of the chain a hydroxy group and at the other end of the chain the C$_8$ to C$_{28}$ alkyl group of the fatty alcohol.

Preferred ethoxylated fatty alcohols (d) have a degree of ethoxylation from about 90 to about 110. It is very particularly preferred if ethoxylated fatty alcohols (d) having a degree of ethoxylation of about 100 are employed.

In a further very particularly preferred embodiment, an agent for coloring and/or lightening keratinic fibers is characterized in that it contains as (an) ethoxylated fatty alcohol(s) (d) having a degree of ethoxylation from about 80 to about 120 one or more compounds of formula (I)

$$R1\!-\!\!\left[\!O\!-\!CH_2\!-\!CH_2\!\right]_n\!\!-\!OH \qquad (I)$$

in which R1 denotes a saturated or unsaturated, unbranched or branched C$_8$ to C$_{24}$ alkyl group, preferably a saturated, unbranched C$_{16}$ or C$_{18}$ alkyl group, and
n denotes an integer from about 80 to about 120, preferably an integer from about 90 to about 110, and particularly preferably the number 100.

In the course of the work leading to this disclosure it has emerged that, surprisingly, the degree of ethoxylation of the ethoxylated fatty alcohol (d) substantially influences the ability of the agent to reduce ammonia odor. For this reason, it is particularly preferred if one or more ethoxylated fatty alcohols having a very specific degree of ethoxylation are employed as (an) ethoxylated fatty alcohol(s).

A particularly advantageous and thus explicitly very particularly preferred agent for coloring and/or lightening keratinic fibers is characterized in that it contains as (an) ethoxylated fatty alcohol (d) one or more compounds from the group of hexadecan-1-ol (hexadecyl alcohol, cetyl alcohol, palmityl alcohol) ethoxylated with 90 EO,
hexadecan-1-ol (hexadecyl alcohol, cetyl alcohol, palmityl alcohol) ethoxylated with 91 EO,
hexadecan-1-ol (hexadecyl alcohol, cetyl alcohol, palmityl alcohol) ethoxylated with 92 EO,
hexadecan-1-ol (hexadecyl alcohol, cetyl alcohol, palmityl alcohol) ethoxylated with 93 EO,
hexadecan-1-ol (hexadecyl alcohol, cetyl alcohol, palmityl alcohol) ethoxylated with 94 EO,
hexadecan-1-ol (hexadecyl alcohol, cetyl alcohol, palmityl alcohol) ethoxylated with 95 EO,
hexadecan-1-ol (hexadecyl alcohol, cetyl alcohol, palmityl alcohol) ethoxylated with 96 EO,
hexadecan-1-ol (hexadecyl alcohol, cetyl alcohol, palmityl alcohol) ethoxylated with 97 EO,
hexadecan-1-ol (hexadecyl alcohol, cetyl alcohol, palmityl alcohol) ethoxylated with 98 EO,
hexadecan-1-ol (hexadecyl alcohol, cetyl alcohol, palmityl alcohol) ethoxylated with 99 EO,
hexadecan-1-ol (hexadecyl alcohol, cetyl alcohol, palmityl alcohol) ethoxylated with 100 EO,
hexadecan-1-ol (hexadecyl alcohol, cetyl alcohol, palmityl alcohol) ethoxylated with 101 EO,
hexadecan-1-ol (hexadecyl alcohol, cetyl alcohol, palmityl alcohol) ethoxylated with 102 EO,
hexadecan-1-ol (hexadecyl alcohol, cetyl alcohol, palmityl alcohol) ethoxylated with 103 EO,
hexadecan-1-ol (hexadecyl alcohol, cetyl alcohol, palmityl alcohol) ethoxylated with 104 EO,
hexadecan-1-ol (hexadecyl alcohol, cetyl alcohol, palmityl alcohol) ethoxylated with 105 EO,
hexadecan-1-ol (hexadecyl alcohol, cetyl alcohol, palmityl alcohol) ethoxylated with 106 EO,
hexadecan-1-ol (hexadecyl alcohol, cetyl alcohol, palmityl alcohol) ethoxylated with 107 EO,
hexadecan-1-ol (hexadecyl alcohol, cetyl alcohol, palmityl alcohol) ethoxylated with 108 EO,
hexadecan-1-ol (hexadecyl alcohol, cetyl alcohol, palmityl alcohol) ethoxylated with 109 EO,
hexadecan-1-ol (hexadecyl alcohol, cetyl alcohol, palmityl alcohol) ethoxylated with 110 EO,
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO, octadecan-1-ol (octadecyl alcohol, stearyl alcohol) ethoxylated with 109 EO, octadecan-1-ol (octadecyl alcohol, stearyl alcohol) ethoxylated with 110 EO.

The ammonia odor of the agents according to the present disclosure for coloring and/or lightening hair can in particular be masked completely during the entire utilization time period when the specially ethoxylated fatty alcohols (d) are employed in special quantity ranges.

In a further preferred embodiment, an agent for coloring and/or lightening keratinic fibers is therefore characterized in that it contains one or more ethoxylated fatty alcohols (d) having a degree of ethoxylation from about 80 to about 120 in a total quantity from about 0.1 to about 1.5 wt %, preferably from about 0.2 to about 1.2 wt %, more preferably from about 0.3 to about 0.9 wt %, and particularly preferably from about 0.4 to about 0.8 wt %, based on the total weight of the ready-to-use agent.

Lastly, as a fifth formulation constituent (e) essential to the disclosure, the agents according to the present disclosure contain one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol).

It has emerged in this context that the agents according to the present disclosure are, in particular, particularly suitable when the fatty alcohols (e) employed in them are arachyl alcohol (eicosan-1-ol) and/or behenyl alcohol (docosan-1-ol).

In cosmetic agents that contained one of these two alcohols, or a mixture thereof, it was possible to completely mask the ammonia over a particularly long period of time. In addition, it was possible with these agents to achieve coloring results with outstandingly good fastness properties, in particular good washing fastness and good gray coverage.

In a further preferred embodiment, an agent for coloring and/or lightening keratinic fibers is characterized in that it contains arachyl alcohol (eicosan-1-ol) as a fatty alcohol (e).

In a further preferred embodiment, an agent for coloring and/or lightening keratinic fibers is characterized in that it contains behenyl alcohol (docosan-1-ol) as a fatty alcohol (e).

In a further preferred embodiment, an agent for coloring and/or lightening keratinic fibers is characterized in that it contains arachyl alcohol (eicosan-1-ol) and behenyl alcohol (docosan-1-ol) as a fatty alcohol (e).

In a further very particularly preferred embodiment, an agent for coloring and/or lightening keratinic fibers is characterized in that it contains arachyl alcohol (eicosan-1-ol) and/or behenyl alcohol (docosan-1-ol) as a fatty alcohol (e).

The fastness properties of the color results achievable with the agents according to the present disclosure can in particular be further optimized when the fatty alcohols (e) are also employed in special quantity ranges.

In a further particularly preferred embodiment, an agent for coloring and/or lightening keratinic fibers is therefore characterized in that it contains the fatty alcohol(s) (e) from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol) in a total quantity from about 0.7 to about 5.0 wt %, preferably from about 0.9 to about 4.0 wt %, more preferably from about 1.1 to about 3.0 wt %, and particularly preferably from about 1.2 to about 2.8 wt %, based on the total weight of the ready-to-use agent.

In a further particularly preferred embodiment, an agent according to the present disclosure is characterized in that it contains, in a cosmetic carrier, (a) ammonia,
(b) monoethanolamine,
(c) potassium hydroxide,
(d) one or more ethoxylated fatty alcohols having a degree of ethoxylation from about 80 to about 120 that are selected from the group of:
  octadecan-1-ol (octadecyl alcohol, stearyl alcohol) ethoxylated with 90 EO,
  octadecan-1-ol (octadecyl alcohol, stearyl alcohol) ethoxylated with 91 EO,
  octadecan-1-ol (octadecyl alcohol, stearyl alcohol) ethoxylated with 92 EO,
  octadecan-1-ol (octadecyl alcohol, stearyl alcohol) ethoxylated with 93 EO,
  octadecan-1-ol (octadecyl alcohol, stearyl alcohol) ethoxylated with 94 EO,
  octadecan-1-ol (octadecyl alcohol, stearyl alcohol) ethoxylated with 95 EO,
  octadecan-1-ol (octadecyl alcohol, stearyl alcohol) ethoxylated with 96 EO,
  octadecan-1-ol (octadecyl alcohol, stearyl alcohol) ethoxylated with 97 EO,
  octadecan-1-ol (octadecyl alcohol, stearyl alcohol) ethoxylated with 98 EO,
  octadecan-1-ol (octadecyl alcohol, stearyl alcohol) ethoxylated with 99 EO,
  octadecan-1-ol (octadecyl alcohol, stearyl alcohol) ethoxylated with 100 EO,
  octadecan-1-ol (octadecyl alcohol, stearyl alcohol) ethoxylated with 101 EO,
  octadecan-1-ol (octadecyl alcohol, stearyl alcohol) ethoxylated with 102 EO,
  octadecan-1-ol (octadecyl alcohol, stearyl alcohol) ethoxylated with 103 EO,
  octadecan-1-ol (octadecyl alcohol, stearyl alcohol) ethoxylated with 104 EO,
  octadecan-1-ol (octadecyl alcohol, stearyl alcohol) ethoxylated with 105 EO,
  octadecan-1-ol (octadecyl alcohol, stearyl alcohol) ethoxylated with 106 EO,
  octadecan-1-ol (octadecyl alcohol, stearyl alcohol) ethoxylated with 107 EO,
  octadecan-1-ol (octadecyl alcohol, stearyl alcohol) ethoxylated with 108 EO,
  octadecan-1-ol (octadecyl alcohol, stearyl alcohol) ethoxylated with 109 EO,
  octadecan-1-ol (octadecyl alcohol, stearyl alcohol) ethoxylated with 110 EO,
(e) behenyl alcohol (docosan-1-ol).

In a further particularly preferred embodiment, an agent according to the present disclosure is characterized in that it contains, in a cosmetic carrier, (a) ammonia,
(b) 2-amino-2-methylpropanol,
(c) potassium hydroxide,
(d) one or more ethoxylated fatty alcohols having a degree of ethoxylation from about 80 to about 120 that are selected from the group of:
  octadecan-1-ol (octadecyl alcohol, stearyl alcohol) ethoxylated with 90 EO,
  octadecan-1-ol (octadecyl alcohol, stearyl alcohol) ethoxylated with 91 EO,
  octadecan-1-ol (octadecyl alcohol, stearyl alcohol) ethoxylated with 92 EO, octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO,
(e) behenyl alcohol (docosan-1-ol).

In a further particularly preferred embodiment, an agent according to the present disclosure is characterized in that it contains, in a cosmetic carrier,
(a) ammonia,
(b) monoethanolamine,
(c) potassium hydroxide,
(d) one or more ethoxylated fatty alcohols having a degree of ethoxylation from about 80 to about 120 that are selected from the group of:
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO,
(e) arachyl alcohol (eicosan-1-ol).

In a further particularly preferred embodiment, an agent according to the present disclosure is characterized in that it contains, in a cosmetic carrier,
(a) ammonia,
(b) 2-amino-2-methylpropanol,
(c) potassium hydroxide,
(d) one or more ethoxylated fatty alcohols having a degree of ethoxylation from about 80 to about 120 that are selected from the group of:
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO, octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO,
(e) arachyl alcohol (eicosan-1-ol).

In a further particularly preferred embodiment, an agent according to the present disclosure is characterized in that it contains, in a cosmetic carrier,
(a) ammonia,
(b) monoethanolamine,
(c) potassium hydroxide,
(d) one or more ethoxylated fatty alcohols having a degree of ethoxylation from about 80 to about 120 that are selected from the group of:
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 BO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO,
(e) arachyl alcohol (eicosan-1-ol) and behenyl alcohol (docosan-1-ol).

In a further particularly preferred embodiment, an agent according to the present disclosure is characterized in that it contains, in a cosmetic carrier,
(a) ammonia,
(b) 2-amino-2-methylpropanol,
(c) potassium hydroxide,
(d) one or more ethoxylated fatty alcohols having a degree of ethoxylation from about 80 to about 120 that are selected from the group of:
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO,
(e) arachyl alcohol (eicosan-1-ol) and behenyl alcohol (docosan-1-ol).

Because the agents according to the present disclosure are agents for oxidative coloring of hair, they therefore additionally contain oxidation dye precursors in order to form the dyes.

Categorized among the oxidation dye precursors are oxidation dye precursors of the developer type and of the coupler type. Particularly suitable oxidation dye precursors of the developer type are selected from at least one compound from the group of p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and physiologically acceptable salts thereof.

Particularly suitable oxidation dye precursors of the coupler type are selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or physiologically acceptable salts thereof.

In a preferred embodiment, the agents according to the present disclosure additionally contain one or more oxidation dye precursors in a total quantity from about 0.01 to about 4.0 wt %, preferably from about 0.1 to about 3.5 wt %, more preferably from about 0.6 to about 3.1 wt %, and very particularly preferably from about 1.2 to about 2.2 wt %, based on the total weight of the ready-to-use agent.

In a further preferred embodiment, the agents according to the present disclosure additionally contain at least one further substantive dye. Substantive dyes can be subdivided into anionic, cationic, and nonionic substantive dyes. The substantive dyes are preferably selected from nitrophenylenediamines, nitroaminophenols, azo dyes, anthraquinones, triarylmethane dyes, or indophenols, and physiologically acceptable salts thereof. The additional substantive dyes are respectively employed preferably in a proportion from about 0.001 to about 2 wt %, based on the total utilization preparation.

Preferred anionic substantive dyes are the compounds known by the international designations resp. trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue.

Preferred cationic substantive dyes are cationic triphenylmethane dyes such as, for example, Basic Blue 7, Basic Blue 26, Basic Violet 2, and Basic Violet 14, aromatic systems that are substituted with a quaternary nitrogen group, for example Basic Yellow 57, Basic Red 76, Basic Blue 99, Basic Brown 16, and Basic Brown 17, cationic anthraquinone dues such as HC Blue 16 (Bluequat B), as well as substantive dyes which contain a heterocycle that comprises at least one quaternary nitrogen atom, in particular Basic Yellow 87, Basic Orange 31, and Basic Red 51. The cationic substantive dyes that are marketed under the Arianor® trademark are likewise preferred cationic substantive dyes according to the present disclosure.

Nonionic nitro and quinone dyes, and neutral azo dyes, are particularly suitable as nonionic substantive dyes. Preferred nonionic substantive dyes are the compounds known by the international designations resp. commercial names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropylamino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

In addition to the ingredients recited above, the agents according to the present disclosure can furthermore contain the ingredients usual for oxidative coloring agents.

Formation of the dyes in oxidative coloring agents occurs only under the influence of an oxidizing agent; hydrogen peroxide is usually used for this. In a preferred embodiment, hydrogen peroxide is used as an aqueous solution. Oxidizing agent preparations preferred according to the present disclosure are characterized in that they contain about 1.0 to about 23.0 wt %, more preferably about 2.5 to about 21.0 wt %, particularly preferably about 4.0 to about 20.0 wt %, and very particularly preferably about 5.0 to about 18.0 wt % hydrogen peroxide (calculated as 100-percent $H_2O_2$).

It has proven to be advantageous if the oxidizing agent preparations according to the present disclosure additionally contain at least one stabilizer or complexing agent in order to stabilize the hydrogen peroxide. Particularly preferred stabilizers are, in particular, EDTA and EDDS, and phosphonates, in particular 1-hydroxyethane-1,1-diphosphonate (HEDP) and/or ethylenediaminetetramethylenephosphonate (EDTMP) and/or diethylenetriaminepentamethylenephosphonate (DTPMP) resp. sodium salts thereof.

Furthermore, the agents according to the present disclosure can additionally contain polymers and/or thickeners. Cationic, anionic, and/or zwitterionic polymers can be used as polymers. Examples of suitable anionic polymers are obtainable commercially, for example, under the trade names Carbopol® or Rheothik® 11-80. The polymers marketed under the INCI name Acrylates Copolymers are also suitable anionic polymers. A preferred commercial product is, for example, Aculyn® 33 of the Rohm & Haas company. Further preferred anionic polymers are marketed by the Rohm & Haas company under the trade name Aculyn® 22 and by the National Starch company under the trade names Structure® 2001 and Structure® 3001.

Suitable additionally usable cationic polymers are, for example, Polyquaternium-24 (commercial product e.g. Quatrisoft® LM 200), Copolymer 845 (manufacturer: ISP), Gaffix® VC 713 (manufacturer: ISP), Gafquat® ASCP 1011, Gafquat® HS 110, Luviquat® 8155, and Luviquat® MS 370.

As naturally occurring thickening agents, nonionic guar gums such as, for example, both modified (e.g. Jaguar® HP8, Jaguar® HP60, Jaguar® HP120, Jaguar® DC 293, and Jaguar® HP105) and unmodified guar gums (e.g. Jaguar® C) can be used. Further suitable thickening agents are scleroglucan gums or xanthan gums, gums, gum arabic, ghatti gum, karaya gum, tragacanth gum, carrageenan gum, agar-agar, locust bean flour, pectins, alginates, starch fractions and derivatives such as amylose, amylopectin, and dextrins, cellulose derivatives, e.g. methyl cellulose, carboxyalkyl celluloses, and hydroxyalkyl celluloses.

Further anionic, cationic, or amphoteric surfactants can likewise be contained in the agents according to the present disclosure. Preferred anionic surfactants are alkyl sulfates, alkyl ether sulfates, and ethercarboxylic acids having about 10 to about 18 carbon atoms in the alkyl group and up to about 12 glycol ether groups in the molecule. Particularly preferred amphoteric surfactants are N-cocalkylaminopropionate, cocacylaminoethylaminopropionate, and $C_{12}$ to $C_{18}$ acylsarcosine.

Preferred additionally contained cationic surfactants are, for example, ammonium halides, in particular chlorides and bromides, such as alkyltrimethylammonium chlorides, dialkyldimethylammonium chlorides, and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, as well as the imidazolium compounds known by the INCI names Quaternium-27 and Quaternium-83.

The agents according to the present disclosure can moreover contain further active agents, adjuvants, and additives, for example nonionic polymers, silicones, cationic polymers, structuring agents, solvents and solubilizers, fiber-structure-improving active agents, defoamers such as silicones, anti-dandruff active agents, protein hydrolysates, vegetable oils such as macadamia nut oil, kukui nut oil, palm oil, amaranth seed oil, peach kernel oil, avocado oil, olive oil, coconut oil, rapeseed oil, sesame oil, jojoba oil, soy oil, peanut oil, evening primrose oil, and tea tree oil, light-protection agents, substances for adjusting pH, for example usual acids, in particular edible acids, vitamins, provitamins, and vitamin precursors, plant extracts, consistency agents, waxes, further swelling and penetration substances, luster agents such as ethylene glycol mono- and distearate as well as PEG-3 distearate, propellants such as propane/butane mixtures, $N_2O$, dimethyl ether, $CO_2$, and air, and antioxidants.

One skilled in the art will arrive at a selection of these further substances in accordance with the desired properties of the agents.

With regard to further optional components, as well as the quantities of those components used, reference is made expressly to the relevant manuals known to one skilled in the art, e.g. Kh. Schrader, Grundlagen and Rezepturen der Kosmetika [Cosmetics fundamentals and formulations], 2nd ed., Hüthig Buch Verlag, Heidelberg, 1989.

The additional active agents and adjuvants are employed in the agents according to the present disclosure preferably in quantities respectively from about 0.0001 to about 10 wt %, in particular from about 0.0005 to about 5 wt %, based on the total weight of the utilization mixture.

Coloring and lightening processes on keratin fibers usually proceed in an alkaline environment. In order to minimize stress on the keratin fibers and also on the skin, however, it is not desirable to establish too high a pH. It is therefore preferred if the pH of the ready-to-use agent is between about 6 and about 12, in particularly between about 7 and about 10.5. The pH values for purposes of the present disclosure are pH values that were measured at a temperature of about 22° C.

The agents according to the present disclosure are agents for oxidative coloring and/or lightening of hair. In ready-to-use agents, the oxidation dye precursors react with the oxidizing agent, accompanied by formation of the actual dyes. The agents according to the present disclosure are therefore formulated as multi-component agents, in most cases as two-component agents. The first component contains the oxidation dye precursors and the alkalizing agent (preparation A), which is mixed shortly before utilization with a second component containing the oxidizing agent (preparation B). The two components are usually mixed with one another at a ratio from about 1:3 to about 3:1. This mixture of the component containing color cream/alkalizing agent (preparation A) and the component containing oxidizing agent (preparation B) is referred to as the "utilization mixture" or the "ready-to-use agent." All quantity indications with reference to the "ready-to-use agent" refer to the ready-to-use mixture of the component containing color cream/alkalizing agent and the component containing oxidizing agent.

A further subject of the present disclosure is therefore a ready-to-use agent for coloring and/or lightening keratinic fibers, which is characterized in that it is produced immediately before utilization by mixing preparations (A) and (B), wherein preparation (A) is an agent of the first subject of the disclosure, preparation (B) is an agent that contains hydrogen peroxide in a cosmetic carrier, and the ready-to-use agent produced by mixing preparations (A) and (B) contains hydrogen peroxide in a quantity from about 0.5 to about 8.0 wt %, preferably about 1.5 to about 6.5 wt %, more preferably about 2.2 to about 4.5 wt %, and particularly preferably about 3.0 to about 3.6 wt %, (calculated as 100-percent hydrogen peroxide), based on the total weight of the ready-to-use agent.

A further subject of the present disclosure is a method for coloring and/or lightening keratinic fibers which is characterized in that if desired, a pretreatment agent M1 is applied onto the fibers, then a coloring and/or lightening agent M2 is utilized on the fibers, a further agent M3 being added if desired to the agent M2 before utilization, said agent M2 is rinsed off the fibers after a time from about 5 to about 30 minutes, and after treatment, optionally a post-treatment agent M4 is applied onto the fibers and is rinsed off again after a contact time from about 2 to about 25 minutes, the agent M2 being an agent according to the present disclosure.

The statements made about the agents according to the present disclosure apply mutatis mutandis with regard to further preferred embodiments of the methods and uses according to the present disclosure.

ILLUSTRATIVE EXAMPLES

The present disclosure is now illustrated by the following non-limiting examples. It should be noted that various changes and modifications can be applied to the following examples and processes without departing from the scope of this disclosure, which is defined in the appended claims.

Therefore, it should be noted that the following examples should be interpreted as illustrative only and not limiting in any sense.

1. Coloring Tests and Determination of Washing Fastness Values

The following formulations were produced:

| Formulation constituents (color cream) | V1 (wt %) | E1 (wt %) |
|---|---|---|
| Cetyl alcohol | 8.10 | 5.70 |
| Lanette 22 (INCI: Behenyl Alcohol) | — | 2.40 |
| Wacker Belsil ADM 1650 (INCI: Amodimethicone) | 0.5 | 0.5 |
| Eumulgin B 1 (INCI: Ceteareth-12) | 1.2 | — |
| Eumulgin B 3 (INCI: Ceteareth-30) | — | 1.2 |
| Eumulgin B 2 (INCI: Ceteareth-20) | 0.6 | — |
| Brij S 100 PA (Stearyl alcohol ethoxylated (100 EO)) | — | 0.6 |
| Cutina QMS (INCI: Glyceryl Stearate) | 0.6 | 0.6 |
| Genamin STAC (INCI: Steartrimonium Chloride) | 1.75 | 1.75 |
| Propylene glycol | 6.0 | 6.0 |
| p-Toluylenediamine sulfate | 1.50 | 1.50 |
| Resorcinol | 0.58 | 0.58 |
| m-Aminophenol | 0.16 | 0.16 |
| 3-Amino-2-methylamino-6-methoxypyridine | 0.05 | 0.05 |
| Potassium hydroxide (50%) | 0.7 | 0.7 |
| Ethylenediaminetetraacetic acid, tetrasodium salt | 0.20 | 0.20 |
| Sodium sulfite (anhydrous) | 0.30 | 0.30 |
| Vitamin C | 0.05 | 0.05 |
| Product W 37194 ((N,N,N-trimethyl-3-[(1-oxo-2-propenyl)amino]-1-propanaminium chloride, polymer with sodium 2-propenoate) (INCI: Acrylamidopropyltrimonium Chloride/Acrylate Copolymer) 20-wt % aqueous solution | 2.00 | 2.00 |
| Monoethanolamine | 2.00 | 2.00 |
| Ammonia (25-wt % aqueous solution) | 5.80 | 5.80 |
| Perfume | 0.40 | 0.40 |
| Water | to 100 | to 100 |

V1 is a comparison formulation; E1 is a formulation according to the present disclosure.

The color creams were each mixed at a 1:1 ratio with the following oxidizing agent formulation (OX1):

| Formulation constituents | OX1 (wt %) |
|---|---|
| Phosphoric acid, 85% | 0.04 |
| Hydrogen peroxide (50%, aqueous solution) | 12.00 |
| Emulgade F (INCI: Cetearyl Alcohol, PEG-40, Castor Oil, Sodium Cetearyl Sulfate) | 2.10 |
| Sodium benzoate | 0.04 |
| Disodium pyrophosphate | 0.30 |
| Ethylenediaminetetraacetate, disodium salt | 0.15 |
| Water | to 100 |

The utilization mixtures produced in this manner were applied with an Aplicette onto hair strands (yak belly hair) and left there for a time period from 10 to 30 minutes. The utilization mixture was then rinsed out with a shampoo and dried. Dark-brown colors were obtained. The hair strands were then measured colorimetrically (Lab value measurement). The hair strands were then washed 6 times, 12 times, and 18 times, and measured colorimetrically again after each 6, 12, and 18 hair washes (HW). The ΔE value (color distance) was calculated from the Lab values in each case using the following formula:

$$\Delta E = \sqrt{[(L_0-L_x)^2+(a_0-a_x)^2+(b_0+b_x)^2]}$$

$L_0, a_0, b_0$ Colorimetric values after 0 hair washes
$L_x, a_x, b_x$ Colorimetric values after 6, 12, resp. 18 hair washes

TABLE 1

Washing fastness values, utilization time = 10 min

|  | ΔE | Hair washes (HW) |
|---|---|---|
| V1 + OX1 | — | 0 |
| E1 + OX1 | — | 0 |
| V1 + OX1 | 1.80 | 6 |
| E1 + OX1 | 0.96 | 6 |
| V1 + OX1 | 2.53 | 12 |
| E1 + OX1 | 2.22 | 12 |
| V1 + OX1 | 3.11 | 18 |
| E1 + OX1 | 2.74 | 18 |

TABLE 2

Washing fastness values, utilization time = 20 min

|  | ΔE | Hair washes (HW) |
|---|---|---|
| V1 + OX1 | — | 0 |
| E1 + OX1 | — | 0 |
| V1 + OX1 | 1.77 | 6 |
| E1 + OX1 | 1.13 | 6 |
| V1 + OX1 | 2.00 | 12 |
| E1 + OX1 | 1.64 | 12 |
| V1 + OX1 | 1.78 | 18 |
| E1 + OX1 | 1.08 | 18 |

TABLE 3

Washing fastness values, utilization time = 30 min

|  | ΔE | Hair washes (HW) |
|---|---|---|
| V1 + OX1 | — | 0 |
| E1 + OX1 | — | 0 |
| V1 + OX1 | 1.13 | 6 |
| E1 + OX1 | 0.60 | 6 |
| V1 + OX1 | 7.40 | 12 |
| E1 + OX1 | 4.98 | 12 |
| V1 + OX1 | 1.48 | 18 |
| E1 + OX1 | 0.92 | 18 |

The higher the ΔE value, the greater the color distance (color difference) between the respective strands when comparing their color before and after the hair washes. The higher the ΔE value, therefore, the poorer the washing fastness of the corresponding color.

It was found that the washing fastness values of the colors obtained with the formulations according to the present disclosure, irrespective of utilization time (10 min, 20 min, and 30 min), were consistently better than the colors obtained with the comparison formulations.

2. Determining Ammonia Odor During Utilization

The utilization mixtures previously produced (V1+OX1, E1+OX1) were each applied onto the head of a test subject. During the utilization time period, the ammonia odor was evaluated in each case by five trained persons at various points in time (directly after application at 0 min, after 10 min, after 20 min, and after 30 min). The evaluation was performed blind, meaning that the persons who performed the evaluation did not know which formulation they were evaluating at the time. The average of the individual evaluations was calculated in each case.

The ammonia odor was evaluated on a scale from 0 (virtually no odor perceptible) to 10 (very strong ammonia odor).

TABLE 4

| Ammonia odor during utilization (utilization mixture) | | | | |
|---|---|---|---|---|
| | after 0 min | after 10 min | after 20 min | after 30 min |
| V1 + OX1 | 5 | 3.5 | 3.0 | 1.5 |
| E1 + OX1 | 0-1 | 0-1 | 0-1 | 0-1 |

It is evident that the ammonia odor in the context of utilization of the formulation according to the present disclosure, both directly after application of the formulations and after a period of 10 minutes, 20 minutes, and 30, was perceived as appreciably reduced.

3. Determination of Ammonia Odor During Storage

Formulations V1 and E1 were loaded into tubes and stored for several weeks at 40° C. in a storage cabinet. The odor of each of the tubes was evaluated, according to the above-described method, directly when storage began and after 2 weeks, after 4 weeks, after 8 weeks, and after 12 weeks.

The ammonia odor was evaluated on a scale from 0 (virtually no odor perceptible) to 10 (very strong ammonia odor).

TABLE 5

| Ammonia odor of color breams during storage at +40° C. | | |
|---|---|---|
| Color creams | V1 | E1 |
| At initial storage | some ammonia odor perceptible (score 4) | virtually no ammonia odor (score 0-1) |
| After 2 weeks storage (+40° C.) | Ammonia odor clearly perceptible (score 5) | virtually no ammonia odor (score 0-1) |
| After 4 weeks storage (+40° C.) | little ammonia odor (score 2-3) | virtually no ammonia odor (score 0-1) |
| After 8 weeks storage (+40° C.) | minimal ammonia odor (score 1) | virtually no ammonia odor (score 0-1) |
| After 12 weeks storage (+40° C.) | minimal ammonia odor (score 1) | virtually no ammonia odor (score 0-1) |

The ammonia odor was evaluated on a scale from 0 (virtually no odor perceptible) to 10 (very strong ammonia odor).

3. Formulation Examples

| Formulation constituents (color cream) | 1 (wt %) | 2 (wt %) |
|---|---|---|
| Cetyl alcohol | 3.6 | 4.6 |
| Lanette 22 (INCI: Behenyl Alcohol) | 2.4 | 3.0 |
| Paraffinic Liquid | 2.1 | 2.1 |
| Eumulgin B 3 (INCI: Ceteareth-30) | 1.2 | 1.8 |
| Brij S 100 PA (Stearyl alcohol ethoxylated (100 EO)) | 0.6 | 1.0 |
| Cutina GMS (INCI: Glyceryl Stearate) | 0.6 | 0.6 |
| Propylene glycol | 6.0 | 6.0 |
| p-Toluylenediamine sulfate | 1.50 | 1.50 |
| Resorcinol | 0.58 | 0.58 |
| m-Aminophenol | 0.16 | 0.16 |
| 3-Amino-2-methylamino-6-methoxypyridine | 0.05 | 0.05 |
| Potassium hydroxide (50%) | 0.7 | 0.7 |
| Ethylenediaminetetraacetic acid, tetrasodium salt | 0.20 | 0.20 |
| Sodium sulfite (anhydrous) | 0.30 | 0.30 |
| Vitamin C | 0.05 | 0.05 |
| Product W 37194 ((N,N,N-trimethyl-3-[(1-oxo-2-propenyl)amino]-1-propanaminium chloride, polymer with sodium 2-propenoate) (INCI: Acrylamidopropyltrimonium Chloride/Acrylate Copolymer) 20-wt % aqueous solution | 3.75 | 3.0 |
| Monoethanolamine | 2.00 | 2.00 |
| Ammonia (25-wt % aqueous solution) | 5.80 | 5.80 |
| Perfume | 0.40 | 0.40 |
| Water | to 100 | to 100 |

Color creams 1 and 2 were each mixed at a 1:1 ratio with the oxidizing agent formulation (OX) and applied onto hair.

| Formulation constituents | OX (wt %) |
|---|---|
| Sodium benzoate | 0.04 |
| Dipicolinic acid (pyridine-2,6-dicarboxylic acid) | 0.10 |
| Disodium pyrophosphate | 0.10 |
| Potassium hydroxide (50%) | 0.19 |
| Propylene glycol | 0.50 |
| Paraffinum liquidum | 2.00 |
| Cetearyl alcohol | 3.40 |
| Ceteareth-20 | 1.00 |
| Hydrogen peroxide (50% aqueous solution) | 12.20 |
| Water | to 100 |

Both utilization mixtures (color cream 1+OX2, color cream 2+OX2) were notable for a reduced ammonia odor throughout the utilization time period.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

The invention claimed is:

1. An agent for coloring and/or lightening keratinic fibers, in particular human hair, comprising in a cosmetic carrier:
    (a) ammonia,
    (b) one or more alkanolamines from the group of monoethanolamine, 2-amino-2-methylpropanol, and triethanolamine,
    (c) one or more alkalizing agents from the group of potassium hydroxide, sodium hydroxide, sodium silicates, and potassium silicates,
    (d) one or more ethoxylated fatty alcohols having a degree of ethoxylation from about 80 to about 120,
    (e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol).

2. The agent according to claim 1, wherein the ammonia (a) is included in a quantity from about 0.20 to about 1.5 wt % based on the total weight of the ready-to-use agent.

3. The agent according claim 1, wherein the one or more alkanolamines (b) from the group of monoethanolamine, 2-amino-2-methylpropanol, and triethanolamine is included in a total quantity from about 0.2 to about 6.5 wt % based on the total weight of the ready-to-use agent.

4. The agent according to claim 1, further comprising one or more of sodium hydroxide and potassium hydroxide as an alkalizing agent.

5. The agent according to claim 1, wherein the one or more alkalizing agents (c) from the group of potassium hydroxide, sodium hydroxide, sodium silicates, and potassium silicates is included in a total quantity from about 0.1 to about 2.5 wt % based on the total weight of the ready-to-use agent.

6. The agent according to claim 1, wherein the ethoxylated fatty alcohol(s) (d) having a degree of ethoxylation from about 80 to about 120 is one or more compounds of formula (I)

in which R1 denotes a saturated or unsaturated, unbranched or branched $C_8$ to $C_{24}$ alkyl group, preferably a saturated, unbranched $C_{16}$ or $C_{18}$ alkyl group, and n denotes an integer from about 80 to about 120.

7. The agent according to claim 1, wherein the one or more ethoxylated fatty alcohols (d) having a degree of ethoxylation from about 80 to about 120 is included in a total quantity from about 0.1 to about 1.5 wt % based on the total weight of the ready-to-use agent.

8. The agent according to claim 1, wherein the fatty alcohols (e) is/are arachyl alcohol (eicosan-1-ol) and/or behenyl alcohol (docosan-1-ol).

9. The agent according to claim 1, wherein the fatty alcohol(s) (e) is selected from the group consisting of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol) in a total quantity from about 0.7 to about 5.0 wt % based on the total weight of the ready-to-use agent.

10. The agent according to claim 1, characterized in that it includes
    (a) about 0.20 to about 1.5 wt % ammonia,
    (b) about 0.2 to about 6.5 wt % monoethanolamine,
    (c) about 0.1 to about 2.5 wt % potassium hydroxide,
    (d) one or more ethoxylated fatty alcohols having a degree of ethoxylation from about 80 to about 120, and
    (e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), wherein all quantitative indications refer to the total weight of the ready-to-use agent.

11. The agent according to claim 1, characterized in that it includes
    (a) about 0.20 to about 1.5 wt % ammonia,
    (b) about 0.2 to about 6.5 wt % monoethanolamine,
    (c) about 0.1 to about 2.5 wt % sodium hydroxide,
    (d) one or more ethoxylated fatty alcohols having a degree of ethoxylation from about 80 to about 120, and
    (e) one or more fatty alcohols from the group of arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), wherein all quantitative indications refer to the total weight of the ready-to-use agent.

12. The agent according to claim 1, characterized in that it includes
    (a) ammonia,
    (b) monoethanolamine,
    (c) potassium hydroxide,
    (d) one or more ethoxylated fatty alcohols having a degree of ethoxylation from about 80 to about 120 that are selected from the group of:
        octadecan-1-ol (octadecyl alcohol, stearyl alcohol) ethoxylated with 90 EO,
        octadecan-1-ol (octadecyl alcohol, stearyl alcohol) ethoxylated with 91 EO,
        octadecan-1-ol (octadecyl alcohol, stearyl alcohol) ethoxylated with 92 EO,
        octadecan-1-ol (octadecyl alcohol, stearyl alcohol) ethoxylated with 93 EO,
        octadecan-1-ol (octadecyl alcohol, stearyl alcohol) ethoxylated with 94 EO,
        octadecan-1-ol (octadecyl alcohol, stearyl alcohol) ethoxylated with 95 EO,
        octadecan-1-ol (octadecyl alcohol, stearyl alcohol) ethoxylated with 96 EO,
        octadecan-1-ol (octadecyl alcohol, stearyl alcohol) ethoxylated with 97 EO,
        octadecan-1-ol (octadecyl alcohol, stearyl alcohol) ethoxylated with 98 EO,
        octadecan-1-ol (octadecyl alcohol, stearyl alcohol) ethoxylated with 99 EO,
        octadecan-1-ol (octadecyl alcohol, stearyl alcohol) ethoxylated with 100 EO,
        octadecan-1-ol (octadecyl alcohol, stearyl alcohol) ethoxylated with 101 EO,
        octadecan-1-ol (octadecyl alcohol, stearyl alcohol) ethoxylated with 102 EO,
        octadecan-1-ol (octadecyl alcohol, stearyl alcohol) ethoxylated with 103 EO,
        octadecan-1-ol (octadecyl alcohol, stearyl alcohol) ethoxylated with 104 EO,
        octadecan-1-ol (octadecyl alcohol, stearyl alcohol) ethoxylated with 105 EO,
        octadecan-1-ol (octadecyl alcohol, stearyl alcohol) ethoxylated with 106 EO,
        octadecan-1-ol (octadecyl alcohol, stearyl alcohol) ethoxylated with 107 EO,
        octadecan-1-ol (octadecyl alcohol, stearyl alcohol) ethoxylated with 108 EO,
        octadecan-1-ol (octadecyl alcohol, stearyl alcohol) ethoxylated with 109 EO,
        octadecan-1-ol (octadecyl alcohol, stearyl alcohol) ethoxylated with 110 EO, and
    (e) behenyl alcohol (docosan-1-ol).

13. The agent according to claim 1, characterized in that it includes
    (a) ammonia,
    (b) monoethanolamine,
    (c) potassium hydroxide,
    (d) one or more ethoxylated fatty alcohols having a degree of ethoxylation from about 80 to about 120 that are selected from the group of:
        octadecan-1-ol (octadecyl alcohol, stearyl alcohol) ethoxylated with 90 EO,
        octadecan-1-ol (octadecyl alcohol, stearyl alcohol) ethoxylated with 91 EO, octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO, and
(e) arachyl alcohol (eicosan-1-ol) and behenyl alcohol (docosan-1-ol).

14. A ready-to-use agent for coloring and/or lightening keratinic fibers, characterized in that it is produced immediately before utilization by mixing preparations (A) and (B), wherein preparation (A) is an agent of claim 1, preparation (B) is an agent that includes hydrogen peroxide in a cosmetic carrier, and the ready-to-use agent produced by mixing preparations (A) and (B) includes hydrogen peroxide in a quantity from about 0.5 to about 8.0 wt %, (calculated as 100-percent hydrogen peroxide), based on the total weight of the ready-to-use agent.

\* \* \* \* \*

UNITED STATES PATENT AND TRADEMARK OFFICE
CERTIFICATE OF CORRECTION

PATENT NO. : 8,845,758 B2
APPLICATION NO. : 14/102655
DATED : September 30, 2014
INVENTOR(S) : Constanze Neuba and Frank Janssen Page 1 of 1

It is certified that error appears in the above-identified patent and that said Letters Patent is hereby corrected as shown below:

Title Page item (72), line 2, Inventor's Name, change "Frank Jannsen" to --"Frank Janssen"--.

Signed and Sealed this
Sixth Day of January, 2015

Michelle K. Lee
*Deputy Director of the United States Patent and Trademark Office*